ND. S. Patent [19]

Nnadi et al.

[11] 4,048,082
[45] Sept. 13, 1977

[54] ORGANIC LUBRICATING COMPOSITIONS CONTAINING ESTERS OF BENZOTRIAZOLE

[75] Inventors: John C. Nnadi, Glassboro; Phillip S. Landis, Woodbury, both of N.J.

[73] Assignee: Mobil Oil Corporation, New York, N.Y.

[21] Appl. No.: 596,934

[22] Filed: July 17, 1975

[51] Int. Cl.² .................. C10M 1/32; C10M 3/26
[52] U.S. Cl. ......................... 252/51.5 A; 252/392
[58] Field of Search ................. 252/51.5 A, 392

[56] References Cited

U.S. PATENT DOCUMENTS

| 3,219,666 | 11/1965 | Norman | 252/51.5 A |
| 3,413,227 | 11/1968 | Howard | 252/51.5 A |
| 3,632,511 | 1/1972 | Liau | 252/51.5 A |
| 3,969,237 | 7/1976 | Andress | 252/51.5 A X |

Primary Examiner—J. Poer
Assistant Examiner—John F. Niebling
Attorney, Agent, or Firm—Charles A. Huggett; Howard M. Flournoy; Raymond W. Barclay

[57] ABSTRACT

Organic compositions are provided containing anti-rust amounts of esters of adducts of benzotriazole and unsaturated dicarboxylic acids or anhydrides thereof.

8 Claims, No Drawings

ORGANIC LUBRICATING COMPOSITIONS CONTAINING ESTERS OF BENZOTRIAZOLE

BACKGROUND OF THE INVENTION

1. Field of the Invention

This invention relates to organic compositions normally susceptible to oxidative deterioration. More particularly, in one of its aspects, the invention relates to organic compositions, particularly synthetic lubricants and petroleum derived compositions, such as mineral lubricating oils, automotive oils, gear oils, transmission fluids, greases and other forms of organic compositions normally requiring the presence of anti-rust additives.

2. Description of the Prior Art

Prior to the present invention, benzotriazole has been employed in lubricants as a metal deactivator. Benzotraizole maleic anhydride adducts have also been known and are disclosed in "Elisa Shigi and Franca Rocchi," Gass. Chim. Ital. 84, 183 (1955). It is found, however, that these adducts are not effective anti-rust agents inasmuch as they are not oil soluble.

SUMMARY OF THE INVENTION

In accordance with the present invention, we have found that anti-rust properties can be effectively incorporated in organic compositions by including an anti-rust amount of an ester of an adduct of benzotriazole and an unsaturated dicarboxylic acid or anhydride thereof. These ester adducts are soluble in the organic composition, for example, in any of the aforementioned lubricating oils, automotive oils, gear oils, transmission fluids, greases and other forms of organic compositions normally requiring the presence of anti-rust additives and exhibit markedly improved anti-rust properties.

Exemplary of the unsaturated dicarboxylic acids or anhydrides thereof are maleic anhydride, fumaric acid, and acetylene dicarboxylic acid.

The ester adduct can be effectively employed in any amount which is effective for imparting the desired degree of anti-rust properties. In many applications, the ester adduct is effectively employed in an amount from about 0.001% to about 20%, by weight, and preferably in an amount from about 0.5% to about 5%, by weight, of the total weight of the organic composition.

In general, the adduct is made by reacting benzotriazole and the unsaturated acid in a mole ratio of benzotriazole and unsaturated acid of from about 0.5:1 to 2:1. This reaction can be conducted at a temperature from about 80° C to about 250° C and preferably from about 100° C to about 200° C. Esterification of the adduct can be conducted with any of a wide variety of esterifying agents, known to those skilled in the art, and in an amount sufficient to effect esterification. Such esterifying agents, include methyl and higher (alky, alkenyl, arylalkyl, alicylic) alcohols. Other esterifying agents include alcohols obtained by reacting amino alcohols, diols, polyols with acids, acid halides, and anhydrides to form products having at least one unreacted OH group. Still other suitable alcohols for esterification are hydroxy terminated alkylene oxylated phenols, naphthols, esters, amines, amino alcohols and chlorinated poly olefins reacted with amino alcohols. In general, alcohols employed herein can possess from about 1 to about 150 and preferably from about 16 to about 50 carbon atoms. Esterification can be conveniently conducted at a temperature from about 60° C to about 220° C and preferably from about 100° C to about 200° C.

The above-described ester adducts, as previously mentioned, may be incorporated in any lubricating media, which may comprise liquid hydrocarbon oils. These oils may be in the form of either a mineral oil or a synthetic oil or in the form of a grease in which any of the aforementioned oils are employed as a vehicle. In general, mineral oils, employed as the lubricant, or grease vehicle, may be of any suitable lubricating viscosity range, as, for example, from about 45 SSU at 100° F to about 6,000 SSU at 100° F, and, preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethelene glycol, trimethylol propane esters, neopentyl and pentaerythritol esters, di-(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

DESCRIPTION OF SPECIFIC EMBODIMENTS

The following examples and comparative data will serve to illustrate the novel ester adduct of the present invention and the marked improvement in anti-rust properties of organic media, and particularly lubricant compositions, containing them.

EXAMPLE 1

40 grams of an adduct (prepared by reacting 40 grams benzotriazole and 20 grams of maleic anhydride in a steam bath for 5 hours) and 52 grams octadecyl alcohol and 100 grams of a 100 SUS refined pale paraffin oil were heated at a temperature from about 180° C to 200° C for a period of 2 hours and thereafter at 130° C–140° C at xylene reflux, for several hours. Some water was azeotroped off. The xylene was then distilled off under reduced pressure and the residue was filtered. The yield of ester adduct product was 160 grams. Found: % N 1.69.

Example 2

From 105 grams of the benzotriazole-maleic anhydride adduct of Example 1, 160 grams oleyl alcohol and 100 grams of the paraffin oil of Example 1, 250 grams of filtered ester adduct product was obtained. Found: % N 1.64 ester adduct product.

EXAMPLE 3

From 16 grams of the benzotraizole-maleic anhydride adduct of Example 1, 30 grams of $C_{16}/C_{18}$ alfol (straight chain alcohols) and 46 grams of the paraffin oil of Example 1, and treated as in Example 1, 76 grams of filtered ester adduct product was obtained. Found: % N. 1.0.

EXAMPLE 4

From 26 grams of the benzotriazole-maleic anhydride adduct of Example 1, 50 grams $C_{20}/C_{22}$ alfol and 50 grams of the paraffin oil of Example 1, and reacted as in Example 1, 86.5 grams of ester adduct product was obtained. Found: % N 1.35.

EXAMPLE 5

From 18 grams of the benzotriazole-maleic anhydride adduct of Example 1 and 150 grams diol, obtained by reduction of the glycol ester of a polyalkenylsuccinic anhydride (polybutene molecular weight 2,300) and treated as in Example 1, 140 grams of filtered ester adduct product was obtained. Found: % N. 0.71.

EXAMPLE 6

From 0.5 grams of the benzotriazole-maleic anhydride adduct of Example 1 and 40 grams of an ester-alcohol (prepared by reacting $C_{47}$-alkenylsuccinic anhydride with 1,6-hexanediol) and treated as in Example 1, a quantitative yield of ester adduct product was obtained. Found: % N 0.39.

EXAMPLE 7

From 1 gram of the benzotriazole-maleic anhydride adduct of Example 1 and 100 grams of the reaction product of alkenylsuccinic anhydride (polybutene molecular weight 1,300) and an amino alcohol $NH_2C(CH_2OH)_3$, % N 0.49, treated as in Example 1, a quantitative yield of product was obtained. Found: % N 0.64.

EXAMPLE 8

This example illustrates the addition of benzotriazole to other unsaturated carboxylic compounds.

11 grams of fumaric acid was esterified with 54 grams oleyl alcohol using 0.5 grams para-toluene sulfonic acid as catalyst and 50 grams of the paraffin oil of Example 1. The esterified product was then reacted with 12 grams benzotriazole at a temperature from 180° C to 200° C for 4 hours. The reaction mixture was then cooled to 50° C and stirred with 2 grams $Na_2CO_3$ for 1/2 hour. The yield of filtered product was quantitative. Found: % N 4.18.

EXAMPLE 9

The addition of benzotriazole to the dipotassium salt of acetylene dicarboxylic acid was carried out as follows.

15.2 grams acetylene dicarboxylic acid monopotassium salt and 14 grams $K_2CO_3$ were mixed in about 100 cc. dry dimethyl formamide at about 100° C. To this mixture were added 15 grams benzotriazole and the reaction was continued at 100° C for 5 hours. HCl gas was bubbled into the reaction mixture until acidic to about pH 4 and them most of the dimethyl formamide was distilled off under reduced pressure. 56 grams oleyl alcohol and 50 grams of the oil of Example 1 were added to the residue and heated at a temperature from 180° C to 200° C for 4 hours. The ester adduct reaction product was cooled to 50° C and stirred with 4 grams $K_2CO_3$ and then filtered. The yield of product was quantitative. Found: % N 3.53.

EXAMPLE 10

From 4 grams of the benzotriazole-maleic anhydride adduct of Example 1, 50 grams of ethoxylated stearyl-cetyl alcohol and 50 grams of the paraffin oil of Example 1 were reacted at a temperature from about 160° C to about 180° C for 4 hours, as in Example 1. 96 grams of filtered ester adduct product were obtained. Found: % N 0.57.

EXAMPLE 11

From 10 grams of the benzotriazole-maleic anhydride adduct of Example 1, reacted with 50 grams of oil soluble ethoxylated nonylphenol in 20 grams of the paraffin oil of Example 1, 62 grams of filtered ester adduct product was obtained. Found: % N 2.63.

The anti-rust properties of the ester adducts of the present invention were next subjected to a series of tests to evaluate their utility in lubricating oils.

In the following Humidity Chamber Rust Test* the base oil employed was a 150 SSU at 210° F base stock refined paraffinic lubricating oil. To this oil were added 1%, by weight, of the ester adduct products of Examples 1–11, and the days required to show rust were recorded.

*This is a general purpose and rather severe test. It utilizes a humidity chamber operated at 120° F and 97-98% Relative Humidity with an air circulation rate of 150 cubic feet per minute.

The test panels are 2 × 4 × 1/8 inch polished steel plates of SAE 1010 steel of a 10 micron finish.

The test is performed by first cleaning a new panel in naphtha, absolute methanol and xylene in that order. The air dried panel is then dipped in a test formulation for one minute and then "drip-dried" for two hours prior to insertion into the chamber. The panels are suspended in a vertical position within the chamber and can be continuously monitored through the glass dome of the chamber.

The severity of the test can be judged by the rapid rusting rate (1 hour) of a panel coated only with a base stock compared to complete rust inhibition for periods up to 7 days when utilizing an effective rust inhibitor in concentrations of 0.5 to 4.0%.

TABLE
HUMIDITY CHAMBER TEST RESULTS

| Example | Description | Days to Show Mist |
|---|---|---|
|  | Base Oil | <1 |
| 12 | Base Oil + 1% Ex. 1 | >7 |
| 13 | Base Oil + 1% Ex. 2 | >7 |
| 14 | Base Oil + 1% Ex. 3 | >7 |
| 15 | Base Oil + 1% Ex. 4 | >7 |
| 16 | Base Oil + 1% Ex. 5 | 7 |
| 17 | Base Oil + 1% Ex. 6 | 4 |
| 18 | Base Oil + 1% Ex. 7 | 5 |
| 19 | Base Oil + 1% Ex. 8 | >5 |
| 20 | Base Oil + 1% Ex. 9 | 4 |
| 21 | Base Oil + 1% Ex. 10 | 5 |
| 22 | Base Oil + 1% Ex. 11 | 4 |

As will be seen from the foregoing Table, a marked improvement in anti-rust properties of the lubricant is realized employing the novel ester adducts of the present invention as anti-rust additives. The adducts alone, however, have been found not to be soluble in the oil.

Based on the nuclear magnetic reasonance of the adduct, the reaction comprises mostly of the addition of NH portion of benzotriazole across the vinylic double bond of the unsaturated acid, for example, maleic anhydride. This reaction can be illustrated by the following equation:

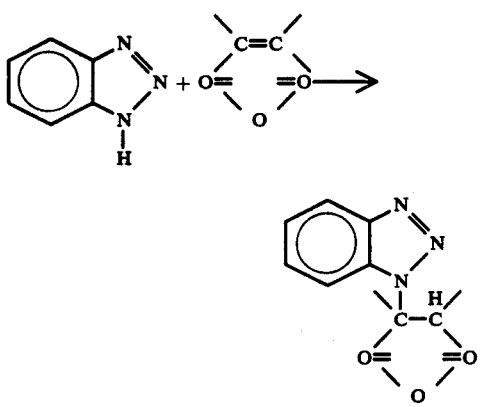

While this invention has been described with reference to preferred compositions and components therefor, it will be understood by those skilled in the art, that departure from preferred embodiments can be effectively made and are within the scope of the specification.

We claim:

1. An organic composition comprising oils of lubricating viscosity or greases prepared therefrom containing a minor anti-rust improving amount of an oil-soluble ester of an adduct of benzotriazole and an unsaturated dicarboxylic acid or anhydride thereof selected from the group consisting essentially of maleic anhydride, fumaric acid and acetylene dicarboxylic acid prepared by reacting said benzotriazole and said unsaturated dicarboxylic acid or anhydride thereof in a mole ratio of from about 0.5:1 to about 2:1 benzotriazole to acid or anhydride at a temperature of from about 80 to about 250° C and thereafter esterifying said adduct.

2. The composition defined in claim 1 wherein the ester adduct is present in an amount from about 0.001% to about 20%, by weight.

3. The composition defined in claim 1 wherein the ester adduct is present in an amount from about 0.5% to about 5%, by weight.

4. The composition defined in claim 1 wherein said composition comprises an oil of lubricating viscosity.

5. The composition defined in claim 1 wherein said composition comprises a grease.

6. The composition defined in claim 1 wherein the unsaturated acid anhydride is maleic anhydride.

7. The composition defined in claim 1 wherein the unsaturated acid is fumaric acid.

8. The composition defined in claim 1 wherein the unsaturated acid is acetylene dicarboxylic acid.

* * * * *